US008601853B2

(12) United States Patent
Degen

(10) Patent No.: US 8,601,853 B2
(45) Date of Patent: Dec. 10, 2013

(54) METHOD AND APPARATUS FOR REDUCING THE SIZE OF AN ENDOPROSTHESIS

(75) Inventor: Nicolas Degen, Beringen (CH)

(73) Assignee: Abbott Laboratories, Abbott Park, IL (US)

( * ) Notice: Subject to any disclaimer, the term of this patent is extended or adjusted under 35 U.S.C. 154(b) by 1064 days.

(21) Appl. No.: 12/323,349

(22) Filed: Nov. 25, 2008

(65) Prior Publication Data
US 2009/0157168 A1 Jun. 18, 2009

Related U.S. Application Data

(60) Provisional application No. 61/014,703, filed on Dec. 18, 2007.

(51) Int. Cl.
B21D 31/00 (2006.01)

(52) U.S. Cl.
USPC ............ 72/377; 72/466.8; 72/370.06; 72/402

(58) Field of Classification Search
USPC ............... 72/466, 466.2, 466.3, 466.4, 466.5, 72/466.6, 466.7, 466.8, 466.9, 465.1, 72/370.01, 370.04, 370.05, 370.06, 72/370.07, 370.08, 292, 377, 378, 402
See application file for complete search history.

(56) References Cited

U.S. PATENT DOCUMENTS 6,702,845 B1 3/2004 Cully et al.
8,006,535 B2 * 8/2011 Righini et al. .................. 72/402

FOREIGN PATENT DOCUMENTS

| EP | 0775472 | 2/2005 |
| EP | 1656908 | 12/2007 |
| WO | WO 2006/117016 | 11/2006 |
| WO | WO 2007/061801 | 5/2007 |
| WO | WO 2009/079189 | 6/2009 |

OTHER PUBLICATIONS

U.S. Appl. No. 61/014,703, filed Dec. 18, 2007, Degen.

* cited by examiner

Primary Examiner — Dana Ross
Assistant Examiner — Matthew G Katcoff
(74) Attorney, Agent, or Firm — Workman Nydegger; Jonathan Feuchtwang

(57) ABSTRACT

An apparatus for collapsing an expandable stent can include a plurality of movable members braided together to form a tubular member or main body portion. The movable members can at least partially define a lumen in the main body portion. The main body portion can be adapted to circumferentially apply an inward force as the diameter of the main body portion is reduced. The diameter of the main body portion can be reduced by moving opposing ends of the main body portion away from each other. An expanded expandable stent can be collapsed by positioning the stent inside the lumen of the main body portion and pulling opposing ends of the main body portion apart. An intermediate layer can be provided between the stent and the main body portion to reduce shear stresses and point forces on the stent.

10 Claims, 1 Drawing Sheet

METHOD AND APPARATUS FOR REDUCING THE SIZE OF AN ENDOPROSTHESIS

CROSS-REFERENCE TO RELATED APPLICATIONS

This application claims the benefit of and priority to U.S. Provisional Patent Application No. 61/014,703, filed Dec. 18, 2007, and entitled "Method And Apparatus For Reducing The Size Of An Endoprosthesis" which is incorporated herein by reference in its entirety.

BACKGROUND OF THE INVENTION

1. The Field of the Invention

The present invention relates to medical devices. More specifically, the present invention relates to a method and apparatus for manufacturing endoprostheses, such as an expandable stent.

2. The Relevant Technology

Stents, grafts, and a variety of other endoprostheses are well known and used in interventional procedures, such as for treating aneurysms, for lining or repairing vessel walls, for filtering or controlling fluid flow, and for expanding or scaffolding occluded or collapsed vessels. Such endoprostheses can be delivered and used in virtually any accessible body lumen of a human or animal, and can be deployed by any of a variety of recognized means. One recognized indication of an endoprosthesis, such as a stent, is for the treatment of atherosclerotic stenosis in blood vessels. For example, after a patient undergoes a percutaneous transluminal coronary angioplasty or similar interventional procedure, a stent is often deployed at the treatment site to improve the results of the medical procedure and reduce the likelihood of restenosis. The stent is configured to scaffold or support the treated blood vessel; if desired, it can also be loaded with a beneficial agent so as to act as a delivery platform to reduce restenosis or the like.

An endoprosthesis, such as a stent, is typically delivered by a catheter delivery system to a desired location or deployment site inside a body lumen of a vessel or other tubular organ. It is useful for the endoprosthesis to be expandable, thereby enabling the endoprosthesis to be of a sufficient size to be introduced into a body lumen of a vessel and thereafter expanded to scaffold or support the treated vessel.

Expandable endoprostheses can be manufactured from a variety of materials and by a variety of methods. For example, a common material used in endoprostheses is a shape memory material (SMM), such as a shape memory alloy (SMA) or shape memory polymer (SMP). SMM is a suitable material due to its properties. SMM's can be "trained" to assume a certain shape after its shape has been deflected, as well as assume a certain shape at a given temperature range. SMM's can have a one-way characteristic, meaning the SMM has a single "trained" shape, or can have a two-way characteristic, meaning the SMM can have more than one "trained" shape. Two-way SMM's can assume different shapes at different temperature ranges.

An endoprosthesis made from a SMM can have advantages. For example, an endoprosthesis, such as a stent, can be manufactured from a piece of tubular SMM material having a diametrical size substantially equal to the desired non-expanded stent size. Thereafter, the unfinished stent can be stretched and "trained" to have a desired expanded orientation through a series of deformations, heating and cooling.

After the stent is "trained" and in the expanded orientation, it is necessary to collapse the stent down to its non-expanded orientation. This can be accomplished by a crimper mechanism with multiple jaws. The jaws of the crimper mechanism can be forced together when the expanded stent is positioned therebetween. As such, the jaws apply force to the expanded stent to collapse the stent. While a crimping mechanism with jaws can be successful in collapsing a stent, this crimping or collapsing process can introduce undesired point forces and surface shear stresses on the stent. Point forces and shear stress on the stent can introduce weaknesses in the stent and reduce the stent's performance and ability to effectively expand. Although the crimping mechanism is useful in collapsing the expanded stent to a non-expanded or collapsed orientation, there remains a need for a device which reduces point forces and shear stresses on stents during their manufacturing process.

BRIEF SUMMARY OF THE INVENTION

The present invention is directed toward a method and apparatus for reducing the size of an endoprosthesis, such as an expandable stent. According to the present invention, a reducing device can be utilized during the manufacturing process, or other procedure, to facilitate collapsing of an expandable stent. The reducing device can be adapted to reduce the point forces and shear stresses induced on the stent due to the crimping or collapsing process.

The reducing device can be adapted to apply a substantially uniform, circumferentially inward force to a stent positioned inside a lumen of the reducing device. In one embodiment, the reducing device can include a plurality of movable members braided together to form a tubular member or main body portion. The movable members can be a plurality of right- and left-handed helical shaped members braided together in a manner which can cause the diameter of the main body portion to increase as opposing ends of the main body portion are moved toward each other. Likewise, as opposing ends of the main body portion are moved away from each other, the diameter of the main body portion can decrease. The plurality of movable members can at least partially define the lumen in the main body portion.

A stent can be positioned in the lumen of the main body portion to collapse the stent. For example, when the stent is positioned in the lumen of the main body portion, the opposing ends of the main body portion can be pulled apart to reduce the diameter of the main body portion. As the diameter of the main body portion is decreased, it can contact the outer surface of the stent. Further pulling of the opposing ends of the main body portion causes a circumferentially inward force to be applied to the stent due to the configuration of the main body portion, specifically, the braided movable members.

The configuration of the movable members can provide a substantially smooth contact surface for contact with the stent. A substantially smooth contact surface can reduce the point forces induced on the stent as the diameter of the main body portion decreases, as opposed to the stent being crimped by jaws of a crimping mechanism. Furthermore, an intermediate layer can be provided between the main body portion and the stent so as to reduce the shear stresses induced on the stent as the diameter of the main body portion is decreased. The intermediate layer can include a single piece of foil lining the main body portion. Alternatively, the intermediate layer can include a plurality of overlapping members configured to move relative to each other.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION

Figure 1:
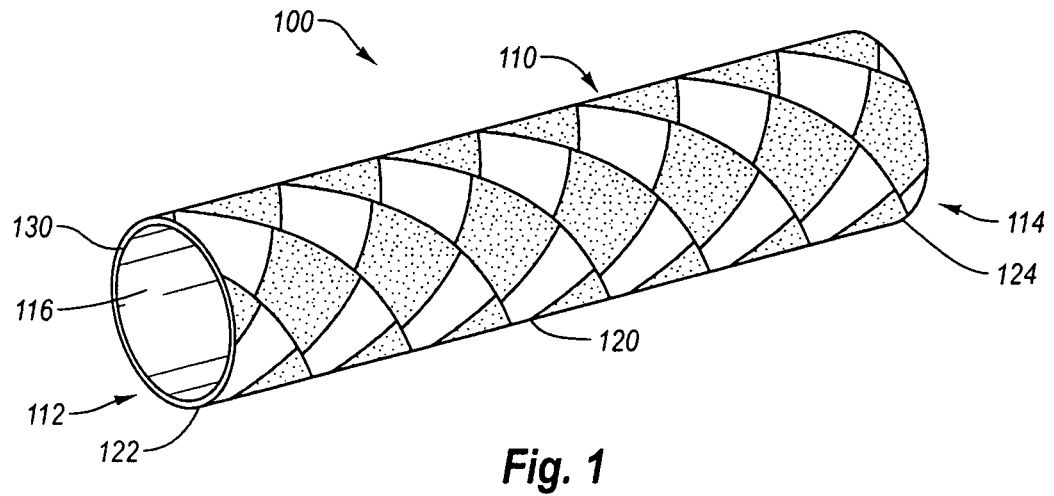
FIG. 1 illustrates a reducing device according to the present invention.

The present invention relates to a method and apparatus for reducing the size of an endoprosthesis during the manufacturing process. The apparatus can be generally referred to as a reducing member. The reducing member can be adapted to apply a substantially even circumferential inward force on the endoprosthesis to reduce its size. The reducing member can be adapted to fit a variety of sizes of endoprostheses, as well as reduce the degree of point forces and shear forces experienced by the endoprosthesis during the reducing step of manufacture.

The reducing member can include a plurality of movable members intertwined or otherwise braided together. The plurality of movable members form a tubular structure and at least partially define a lumen in the reducing member. The configuration of the tubular member enables the reducing member to reduce in diameter as its length increases. The length of the reducing member can be increased by moving one or both of the opposing ends of the reducing member apart. Likewise, the reducing member can thereafter increase in diameter as its length decreases, or in other words, as the ends of the reducing member move toward each other. In this manner, an expanded endoprosthesis, such as an expanded expandable stent, can be reduced in size by being positioned inside the lumen of the reducing member and the ends of the reducing member thereafter pulled apart.

As the ends of the reducing member are pulled apart, the configuration of the tubular member causes the diameter of the reducing member to decrease. The inner surface of the reducing member contacts the outer surface of the endoprosthesis as the diameter of the reducing member decreases. Once in contact in this manner, the ends of the reducing member can be moved further apart to result in further reduction of the reducing member's diameter, thereby applying a circumferential inward force on the expanded endoprosthesis. A circumferential inward force, as opposed to a force only at various crimping points along the circumference of the endoprosthesis, can reduce the magnitude of point forces and shear stress on the endoprosthesis. Reducing point forces and shear stress can reduce the number and degrees of imperfections created in the endoprosthesis during the size reducing portion of the manufacturing process of the endoprosthesis.

An intermediate layer can be provided to reduce the shear stress induced on the endoprosthesis as the reducing member applies a circumferential force on the endoprosthesis. For example, an intermediate layer, such as a layer of foil, can substantially line the inner surface of the tubular member. The intermediate layer can include a plurality of overlapping strips of material, or can be a single piece of material covering a portion or all of the inner surface of the tubular member. In this manner, the intermediate member will be positioned between the endoprosthesis and the tubular member as the endoprosthesis is positioned inside the lumen of the reducing member. The endoprosthesis will contact the intermediate layer, rather than the tubular member, as the diameter of the reducing member is decreased.

As will be appreciated, the apparatus of the present invention can be configured to accommodate for various sizes and lengths of endoprostheses. For example, it will be understood in light of the disclosure provided herein that the size, configuration, and number of the movable members used to form the tubular member can be modified to adapt to various ranges of sizes of endoprostheses.

A description of the reducing member and the method of reducing the size of an expanded endoprosthesis will be described with reference to the illustrations. FIG. 1 is a perspective view of a reducing member 100 according to the present invention. Reducing member 100 can be adapted for use in reducing the size of an endoprosthesis, such as an expandable stent. It should be understood that while a stent is generally referred to herein, as well as illustrated in the figures, with respect to reducing member 100, the principles embodied in the present invention can be applied to various other types of expandable endoprostheses and should not be limited to expandable stents, or more specifically, to the expandable stent disclosed in the figures. Furthermore, while the present invention is useful in the manufacturing process of a stent, it will be understood that the present invention can be utilized in other applications apart from the manufacturing process.

In the illustrated embodiment, reducing member 100 can include a main body portion 110 having a first end 112, an opposing second end 114, and a lumen 116 extending through main body portion 110. Main body portion 110 can be adapted to decrease in diameter as its length is increased. For example, main body portion 110 can be configured such that movement of first end 112 away from second end 114 of main body portion 110 can cause the diameter of lumen 116 to decrease. Likewise, main body portion 110 can be configured such that movement of first end 112 toward second end 114 of main body portion 110 can cause the diameter of lumen 116 to increase.

The lengthening of main body portion 110 thereby decreasing the diameter of lumen 116, and the shortening of main body portion 110 thereby increasing the diameter of lumen 116 is generally discussed herein as reorienting reducing member 100, or otherwise, reorienting main body portion 110. As such, in one embodiment, reducing member 100 can be said to have a first orientation when reducing member 100 has a first diameter and a first length, and can be said to have a second orientation when reducing member 100 has a second diameter which is less than the first diameter and a second length that is greater than the first length.

Reducing member 100 can be adapted to apply a circumferentially inward force to an object, such as an expandable stent, positioned inside of lumen 116 as reducing member 100 is lengthened. For example, main body portion 110 can be adapted to increase and decrease in diameter in a substantially uniform manner along a length of main body portion 110. In this manner, a substantially uniform circumferentially inward force can be applied.

Main body portion 110 can further include a plurality of movable members 120 adapted to enable the reorientation of main body portion 110. Movable members 120 can be adapted to facilitate a substantially uniform reduction in diameter of main body portion 110 as ends of movable members 120 move away from each other. Furthermore, movable members 120 can be adapted to facilitate the application of a circumferentially inward force by main body portion 110 as the diameter of main body portion 110 decreases. Movable members 120 can include a first end 122 and an opposing second end 124. Movable members 120 can be elongated pieces of flexible material, such as an elongated, flat piece of a polymer or metallic material of sufficient size and configuration so as to allow it to flex without plastic deformation throughout the range of desired motion of main body portion 110. In one embodiment, movable members 120 can be flat skeins of nylon-like material. In another configuration, the movable members 120 can be lengths of fiber, wire, thread, filament, strand, cord, or other elongated structures, which can optionally be woven, twisted, or coupled together to perform the function of the movable member.

It will be appreciated that a variety of materials can be used for movable members 120. Furthermore, movable members 120 can have a variety of shapes and configurations without departing from the scope and spirit of the present invention. For example, movable members 120 can be round, rectangular, square, triangular, or some other shape. Furthermore, movable members 120 can be substantially flat. In some embodiments, a plurality of movable members 120 can include eight movable members. In other embodiments, a plurality of movable members 120 can include four movable members. It will be understood that the shape, quantity, and material of movable members 120 can influence the performance and behavioral characteristics of reducing member 100. As such, the shape, quantity and material of movable members 120 can be modified to achieve a desired characteristic of reducing member 100.

According to one configuration, individual movable members 120 can have a generally helical shape with respect to main body portion 110. In one embodiment, movable members 120 can include a plurality of right-handed and left-handed helical shaped movable members. The plurality of right- and left-handed helical members can be weaved or otherwise intertwined together to form the generally tubular shape of main body portion 110. In one embodiment of the present invention, the plurality of movable members 120 can be intertwined through a biaxial braid. In one embodiment, braided movable members 120 can form a tubular member. In this embodiment, the tubular member is an example of main body portion 110. The braided nature of movable members 120 can provide a substantially smooth inner surface for contact with a stent positioned inside lumen 116. In this manner, the degree of point forces induced on a stent positioned inside lumen 116 can be reduced as the diameter of lumen 116 or main body portion 110 is decreased.

Movable members 120 can be configured such that movement of the first end 122 of a movable member 120 toward the second end 124 of the movable member 120 increases the radius of the helical while reducing the pitch of the helical. Likewise, as the first end 122 of the movable member 120 is moved away from the second end 124 of the movable member 120, the radius of the helical is decreased and the pitch of the helical is increased. In this manner, with movable members 120 braided together, movement of first ends 122 toward second ends 124 can cause the individual helical shaped movable members 120 to decrease in pitch but increase in radius, thus resulting collectively in an increase in diameter of main body portion 110. Likewise, movement of first ends 122 away from second ends 124 can cause the individual helical shaped movable members 120 to increase in pitch but decrease in radius, thus resulting collectively in a decrease in diameter of main body portion 110

Intertwining of movable members 120 can create an interrelationship between movable members 120. At least one aspect of the interrelationship of movable members 120 can include the result that movement of a single movable member, i.e. movement of a first end of the single movable member toward or away from a second end of the single movable member, can influence or otherwise cause movement of at least one other movable member. Furthermore, in some cases, movement of a single movable member in this manner can cause movement in a majority of the movable members; 120 yet in other cases, movement of a single movable member can influence and cause movement in all of the remaining movable members 120.

First ends 122 of movable members 120 can collectively define at least a portion of first end 112 of main body portion 110. Likewise, second ends 124 of movable members 120 can collectively define at least a portion of second end 114 of main body portion 110. In this manner, movement of first end 112 of main body portion 110 can describe movement of first ends 122 of movable members 120, and movement of second end 114 of main body portion 110 can describe movement of second ends 124 of main body portion 110, and vice versa.

It will be appreciated by one of ordinary skill in the art in view of the disclosure provided herein that reducing member 100 can further include members on opposing ends of main body portion 110 adapted to facilitate movement of first end 112 of main body portion 110 away or towards second end 114 of main body portion 110. For example, handle members can be provided on opposing ends of main body portion 110. In this embodiment, handle members, not shown, can be adapted to be engaged by a user in order to reorient main body portion 110. Handle members can be adapted to be flexible, so as to reduce or increase in diameter correspondingly with the reduction or increase in diameter of main body portion 110. In alternative embodiments, handle members can be rigid and be sized so as to allow a desired or otherwise predefined size of endoprosthesis therein. In this embodiment, main body portion 110 can be adapted such that as first end 112 and second end 114 of main body portion 110 are moved apart, the center portion of main body member 110 decreases in diameter to a greater degree than those portions adjacent first end 112 and second end 114 of main body portion 110.

In one embodiment, first ends 122 of movable members 120 can be pivotally linked to a first handle member, and second ends 124 of movable members 120 can be pivotally linked to a second handle member. In this manner, movement of the first handle member can influence or otherwise cause movement of first ends 122 of movable members 120, and movement of the second handle member can cause movement of second ends 124 of movable members 120. In this embodiment, movement of the first handle member away from the second handle member can cause main body portion 110 or otherwise lumen 116 to decrease in diameter. Likewise, movement of the first handle member toward the second handle member can cause lumen 116 to increase in diameter.

In one embodiment, movable members 120 can be pivotally linked to handle members by a joining means which allows movement between the handle members and movable members 120. For example, in one embodiment, first ends 122 of movable members 120 can be pivotally attached to the first handle member by threading first ends 122 to the first handle member. In another embodiment, the first handle member can include a recess configured to receive at least a portion of first ends 122 of movable members 120 therein, and a pin member placed through a first portion of the first handle member, through a first end of a single movable member, and then through a second portion of the first handle member. In this embodiment, each first end 122 of each movable member 120 can be individually linked to the first handle member as described. Likewise, second ends 124 of movable members 120 can be pivotally linked to the second handle member in a similar fashion as first ends 122 can be linked to the first handle member.

Reducing member 100 can further include an intermediate layer 130. Intermediate layer 130 can be adapted to reduce point forces on an expandable stent, as well as reduce shear forces on the outer surface of the stent, when collapsing the stent during manufacture or other procedure. Intermediate layer 130 can be positioned on the inner surface of main body portion 110 so as to at least partially define lumen 116. Intermediate layer 130 can be a flexible material, such as a thin metallic material. In one embodiment, intermediate layer 130 can be piece of foil made from a suitable metal material. Intermediate layer 130 can be a single piece of material, or can be a plurality of overlapping pieces configured and arranged to move over each other the diameter of the main body portion 110 is reduced. In alternative embodiments, a coating can be placed on the inner surface of main body portion 110 to provide a similar function as intermediate layer 130.

Figure 2:
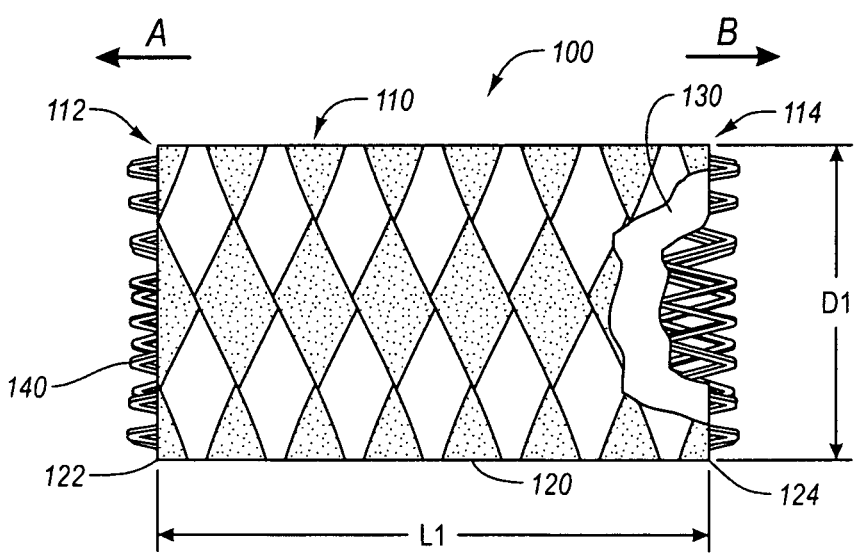
FIG. 2 illustrates a partial cutaway view of the reducing device of FIG. 1 in use in a first orientation according the present invention.

Reference will now be had with respect to the use of reducing member 100 in connection with manufacturing or otherwise processing an expandable stent. FIG. 2 illustrates a partial break away view of reducing member 100 with a stent 140 positioned inside of lumen 116, both reducing member 100 and stent 140 being illustrated in a first orientation. In the illustrated embodiment, stent 140 is in an expanded orientation and intermediate layer 130 can be positioned between main body portion 110 and stent 140.

Figure 3:
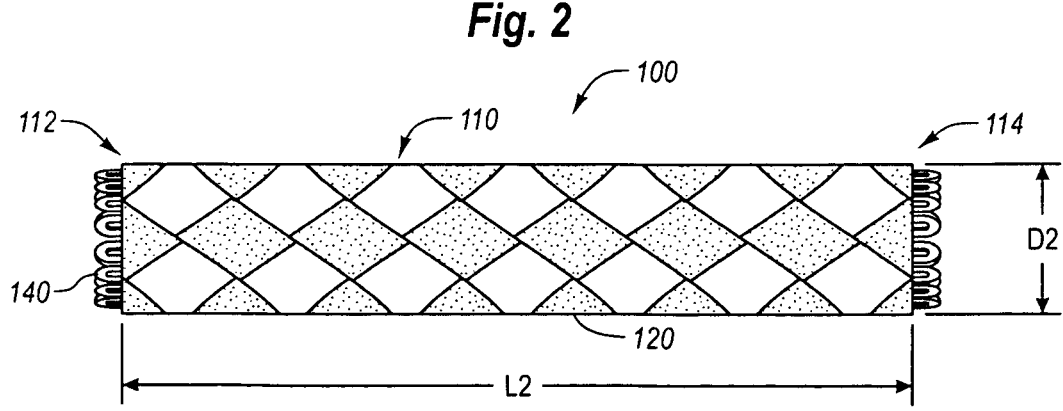
FIG. 3 illustrates the reducing device of FIG. 1 in use in a second orientation according to the present invention.

As shown, reducing member 100 in the first orientation can have a diameter designated as D1 and a length designated as L1. As first end 112 of main body portion 110 is moved in the direction of the arrow designated as A and optionally second end 114 of main body portion 110 is moved in the direction of the arrow designated as B, the diameter of main body portion 110 can be reduced. As the diameter of main body portion 110 is reduced, stent 140 will contact intermediate layer 130, and as a result, will be influenced by main body portion 110. Further reduction of the diameter of main body portion 110 can cause main body portion 110 to apply a circumferentially inward force through intermediate layer 130 to stent 140. A circumferentially inward force on stent 140 can cause stent 140 to reorient from an expanded orientation, as illustrated in FIG. 2, to a non-expanded or otherwise less expanded orientation, such as illustrated in FIG. 3.

Intermediate layer 130 can be adapted to reduce the point forces and shear stresses induced on stent 140. For example, the circumferentially inward force induced by separation of first and second ends 112, 114 of main body portion 110, and thus reduction in diameter of main body portion 110, can be applied to stent 140 through intermediate layer 130. The configuration of intermediate layer 130 can enable stent 140 to slip or otherwise have a degree of movement as main body portion 110 applies the circumferential inward force on stent 140 to collapse or otherwise reduce the diameter of stent 140. As main body portion 110 is applying force on stent 140, intermediate layer 130 can slip or otherwise provide a layer capable of providing a degree of give between the inner surface of main body portion 110 and the outside surface of stent 140. In this manner, the flexibility of intermediate layer 130 can reduce the shear stresses induced on stent 140 as it is being collapsed. Furthermore, the application of circumferentially inward forces by main body portion 110 helps to reduce point forces on stent 140 by distributing the applied force over a larger area. The intermediate layer 130 also helps to reduce point forces by providing a more even layer of contact between main body portion 110 and stent 140.

After stent 140 has been positioned in lumen 116, first end 112 and/or second end 114 of main body portion 110 can be pulled apart to apply force on stent 140. FIG. 3 illustrates reducing member 100 and stent 140 in a second orientation, wherein stent 140 has been collapsed or otherwise reduced in diameter. As illustrated, when in the second orientation, reducing member 100 can have a second diameter designated as D2 and a second length designated as L2. In this embodiment, the first diameter D1 of reducing member 100 is greater than the second diameter D2 of reducing member 100, and the first length L1 of reducing member 100 is less than the second length L2 of reducing member 100.

It will be appreciated that stent 140 may be configured so as to have a greater or lesser degree of change in length than reducing member 100 as reducing member 100 is reoriented between a first and a second orientation, or otherwise reduced in diameter. In this manner, intermediate layer 130 can serve as a buffer layer between main body portion 110 and stent 140 so as to reduce shear stresses and point forces induced on stent 140.

After stent 140 has been collapsed, stent 140 can be cooled utilizing a cooling spray, or alternatively, stent 140 and reducing member 100 can be submersed in a cooling liquid. The configuration of reducing member 100 facilitates the cooling spray coming in contact with stent 140 while reducing member 100 is still in place, as illustrated in FIG. 3. For example, the braiding of movable members 120 can leave gaps between individual movable members 120. The cooling spray, or alternatively, the cooling liquid, can penetrate reducing member 100 through these gaps and contact stent 140.

Cooling of stent 140 during the manufacturing process can be advantageous if the stent material is a SMM. Cooling of a stent made of SMM can enable the stent to retain the "trained" shape for the given temperature range in which the cooling liquid or cooling spray is at, or alternatively, can enable the stent to forget it's "trained" shape which "trained" shape is activated at a higher temperature range than the temperature of the cooling liquid or cooling spray.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for reducing the size of an expandable stent, the method comprising the steps of:
  collapsing an expandable stent utilizing a reducing member that comprises a plurality of movable members intertwined together to form a tubular member, the plurality of moveable members including a plurality of right-handed helically shaped members and a plurality of left-handed helically shaped members extending from a proximal end to a distal end of the reducing member, said reducing member being adapted to apply a circumferential inward force on said stent by positioning a first end of said reducing member away from a second end of said reducing member.

2. A method as recited in claim 1, wherein said collapsing said expandable stent comprises inserting said expandable stent inside said reducing member.

3. A method as recited in claim 1, wherein said collapsing said expandable stent comprises reducing an inner diameter of said reducing member.

4. A method as recited in claim 3, wherein said reducing the inner diameter comprises moving said first end of said reducing device away from said second end of said reducing device.

5. A method for reducing the size of an expandable stent, the method comprising the steps of:
   positioning a separate intermediate layer within a reducing member and between said expandable stent and the reducing member; and
   collapsing the expandable stent utilizing the intermediate layer, which is separate from the reducing member, and the reducing member that comprises a plurality of movable members intertwined together to form a tubular member, the plurality of moveable members including a plurality of right-handed helically shaped members and a plurality of left-handed helically shaped members, said reducing member being adapted to apply a circumferential inward force on said stent by positioning a first end of said reducing member away from a second end of said reducing member.

6. A method as recited in claim 5, wherein said collapsing said expandable stent comprises inserting said expandable stent inside said reducing member.

7. A method as recited in claim 5, wherein said collapsing said expandable stent comprises reducing an inner diameter of said reducing member.

8. A method as recited in claim 7, wherein said reducing the diameter of said lumen comprises moving said first end of said reducing device away from said second end of said reducing device.

9. A method as recited in claim 5, wherein the separate intermediate layer comprises a foil layer.

10. A method as recited in claim 5, wherein the separate intermediate layer comprises a plurality of overlapping pieces and wherein collapsing the expandable stent further comprises moving the plurality of overlapping pieces over each other.

\* \* \* \* \*